(12) United States Patent
Perrego

(10) Patent No.: US 7,354,414 B2
(45) Date of Patent: Apr. 8, 2008

(54) VERTICAL TRACTION ASSEMBLY AND METHOD

(76) Inventor: David W. Perrego, 125 Harborwoods Cir., Safety Harbor, FL (US) 34695

( * ) Notice: Subject to any disclaimer, the term of this patent is extended or adjusted under 35 U.S.C. 154(b) by 1710 days.

(21) Appl. No.: 09/740,169

(22) Filed: Dec. 19, 2000

(65) Prior Publication Data
US 2002/0183675 A1   Dec. 5, 2002

(51) Int. Cl.
*A61F 5/00* (2006.01)
(52) U.S. Cl. .......................... 602/35; 602/32
(58) Field of Classification Search .............. 602/19, 602/32–36, 38, 39; 482/142–144; 606/241; 128/845
See application file for complete search history.

(56) References Cited

U.S. PATENT DOCUMENTS

| | | | |
|---|---|---|---|
| 2,774,349 A | 12/1956 | Judovich | |
| 3,003,498 A * | 10/1961 | Hotas | 602/32 |
| 3,286,708 A | 11/1966 | Gartner | |
| 3,866,914 A | 2/1975 | Jackson | |
| 4,194,500 A | 3/1980 | Grimaldi | |
| 4,205,665 A * | 6/1980 | Burton | 5/610 |
| 4,269,179 A | 5/1981 | Burton | |
| 4,524,763 A | 6/1985 | Eberling, Jr. | |
| 4,569,340 A | 2/1986 | Burton | |
| 4,627,423 A | 12/1986 | Kampner | |
| 4,722,329 A | 2/1988 | Kalvag | |
| 4,890,604 A * | 1/1990 | Nelson | 602/32 |
| 4,890,606 A | 1/1990 | Iams et al. | |
| 4,896,659 A | 1/1990 | Goldish | |
| 5,038,758 A | 8/1991 | Iams et al. | |
| 5,094,228 A | 3/1992 | Reinert | |
| 5,540,643 A | 7/1996 | Fontaine | |
| 5,662,597 A * | 9/1997 | Chitwood | 601/24 |
| 6,123,680 A * | 9/2000 | Brummer | 601/5 |
| 6,217,538 B1 * | 4/2001 | Anderson | 602/33 |

* cited by examiner

Primary Examiner—Quang D. Thanh
(74) Attorney, Agent, or Firm—Neil F. Markva

(57) ABSTRACT

A vertical traction assembly for using gravity to stretch a person's spine comprises a frame structure and a torso harness combination coupled to depend from the frame structure. The harness combination is effective to maintain a person in a vertical traction position after the person dons the harness combination. A focused traction force mechanism is attached to the frame structure for applying a predetermined amount of focused traction pressure directly to a selected location along the spine of the person who is in the vertical traction position. A feature of the traction force mechanism may include its ability to be adjusted to different locations along the frame structure depending on the location of the afflicted area along the spine of the person being treated.

15 Claims, 4 Drawing Sheets

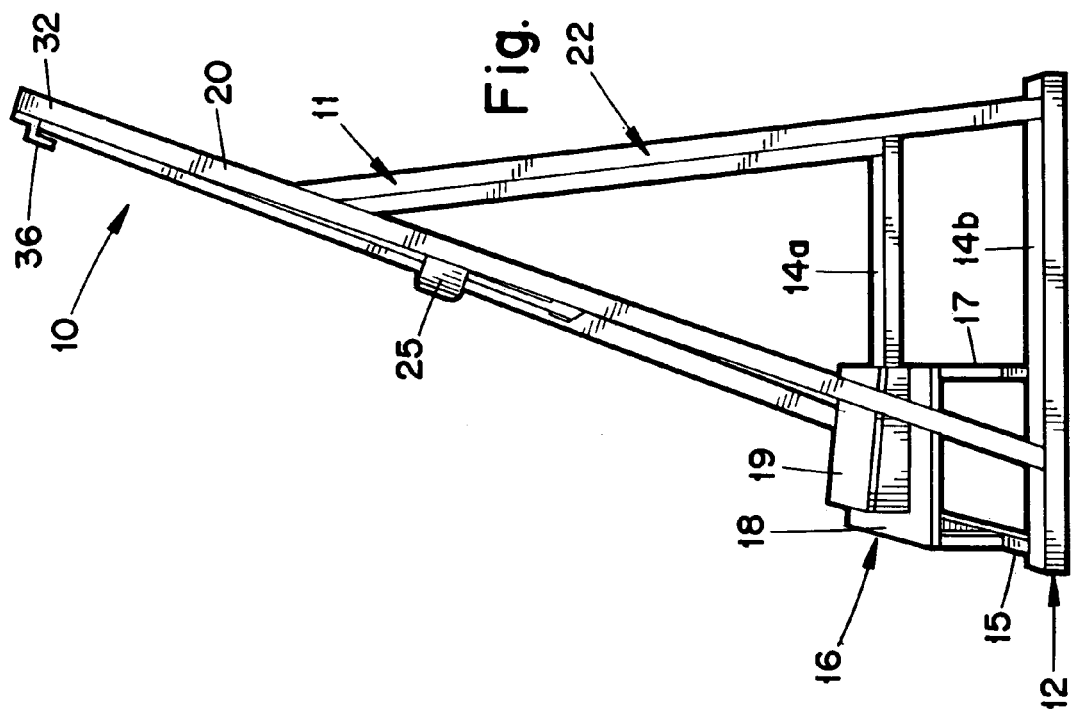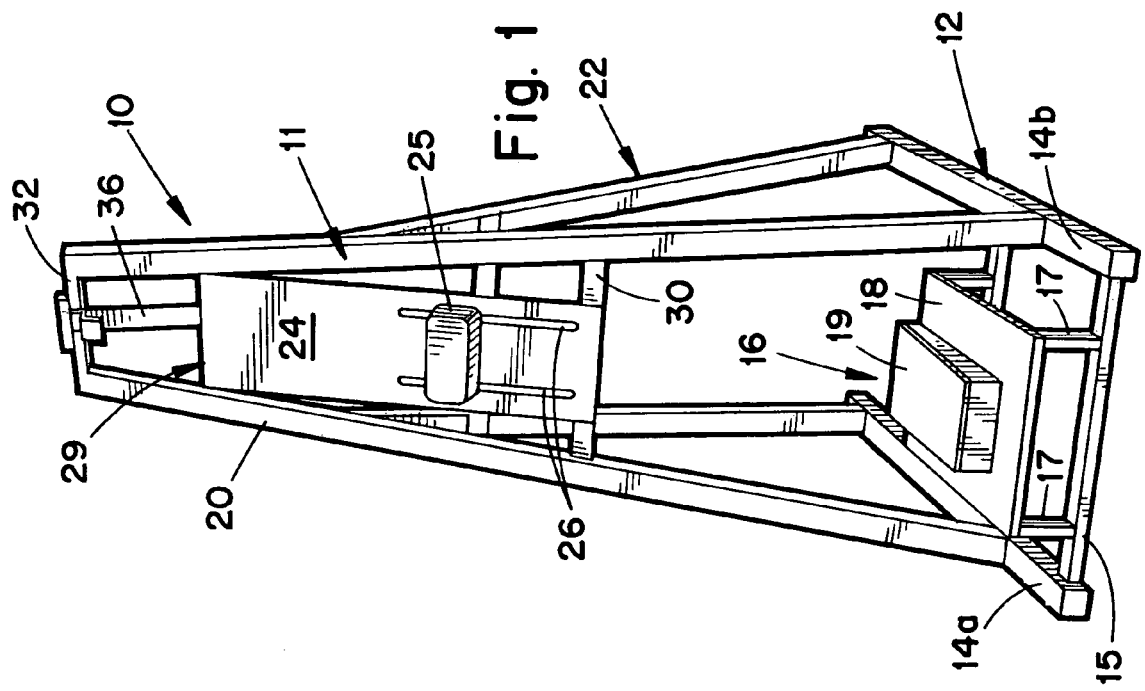

VERTICAL TRACTION ASSEMBLY AND METHOD

FIELD OF THE INVENTION

This invention relates to a therapeutic traction assembly that enables persons being treated to control the time in which a gravity force may be applied to their spine. More particularly, the invention relates to a gravity traction assembly in which a person dons a torso harness depending from a frame structure and voluntarily steps into a suspended traction producing position.

DESCRIPTION OF THE PRIOR ART

Back and leg pain frequently cause temporary and permanent disability of many people. Inflammation regardless of cause (nerve compression, muscle strain, ligament tear, bone spur, arthritis, scar tissue, ruptured or degenerating disks) produces pain in addition to abnormal compression of bones that form the spinal column. Common therapy includes a period of bed rest, and the possible use of anti-inflammatory drugs such as aspirin and steroids. Such therapy is often sufficient to relieve the pain and end the attendant disability for the majority of people. Many, however, do not get lasting relief and may even get worse. The pain may last for a prolonged time of months following its onset despite using therapeutic methods that are helpful to many others.

Numerous known devices may be used to apply various types of traction force to the spinal column of a human. The basic principle of known gravity lumbar traction assemblies is to progressively tilt the patient's body with harness support directed to the low chest area. Under a physician's supervision, the patient controls the progress of the tilt from 30 to 65 degrees, or up to 90 degrees, if necessary. This can be continued on an intermittent basis, independently by the patient once the patient determines his own individual angle of consistent comfort and relief. Approximately 60 percent of the patient's body weight provides the source of gravity pull on the lumbar spine with known devices. And their use appears to include little concern for the amount of time required for treatment to gain lasting results for the patient.

U.S. Pat. No. 2,774,349 discloses a patient fitted with upper and lower body harnesses that are connected to be pulled apart while the patient horizontally reclines on a bed. The patient may control the amount of traction force applied by using a hand control device to operate the machine that pulls the fitted harnesses apart. This early traction device provided an alternative method to a more traditional use of weights in combination with a pulley system to apply pull either to the legs or to the pelvis using a pelvic belt while the patient reclines on a bed.

U.S. Pat. No. 4,205,665 discloses a method and apparatus for supporting a patient with a torso harness while reclining on a bed that may be inclined at a plurality of different inclined positions. More specifically, the patient is to be supported at a reduced angle of up to 30° or more from the horizontal for a significant time of several hours or longer. Treatment might take days or weeks for a patient as the angle of bed inclination incrementally increases toward a vertical position thereby increasing the gravity traction for the patient reclining on it.

U.S. Pat. Nos. 3,286,708; 3,866,914; and 5,662,597 show various gravity traction devices that include an inclined or tiltable support upon which a person may recline using different types of body restraining structures to apply gravity force to relieve back pain.

U.S. Pat. Nos. 4,890,606 and 5,038,753 disclose user controlled devices for decompressing the spine from a seated position. Each device permits leg exercises, and unloads and decompresses the spine and lumbar back by having patients press downwardly with their forearms and hands on opposing sides of a frame structure. A torso harness may be used to maintain continuous decompression of the lower spine between the upward movements executed by the user.

U.S. Pat. No. 5,540,643 describes a back stretching apparatus for creating traction in a user back. The assembly is securable to an apparatus support structure and has two laterally spaced suspension members over which the user raises his arms and pulls upwardly to transfer the user's weight from his legs to the support members. This action causes the weight of the user torso and legs to pull downwardly on the user spine to create traction with all of the user body and leg weight.

U.S. Pat. Nos. 4,194,500; 4,269,179; and 4,524,763 each disclose a gravity spine traction device combining the use of an inclined surface having a frame from which a traction brace depends and girds the torso of patients using the device to receive back stretching treatments. These earlier patents recognize that about 45% of the body weight is in the lower half of the body and have designed upper body harnesses which firmly attach to the patients body just below the rib cage. The supporting frame of a board assembly allows the patient to be suspended on a board so that the weight of the lower body applies tension force to the patient's lumbar spine region. Pat. No. 4,524,763 specifically describes a frame and torso harness system adapted to maintain the thigh portion of the patient's legs in variable angular relation to the long axis of the patient's spine when applying tension traction. The assembly of Pat. No. 4,269,179 requires a block and tackle pulley mechanism to hoist the patient off the floor to a traction force-imposing position. U.S. Pat. No. 4,194,500 assembly includes a pair of spaced apart single foot steps on which the patient stands to don the torso harness and then removes both feet from the steps to suspend from the frame as shown.

U.S. Pat. No. 4,896,659 is directed to a gravity lumbar traction device having a vest worn around the patient's chest with weight supporting arm rests for the elbows and forearms to partially support the patient's weight. The vest depends from a cross bar that is supported in a door frame at a desired level allowing the patient's toes to touch the floor to partially support the patient's weight. A board is optionally placed between the patient and the door frame at the patient's back or front to vary the angle of support for better positioning of the spine, but is unrelated to any specific focal point along the backbone. The board or bar may be moved up or down from the positions shown in the patent drawings depending on the load angle desired. A tilt board is unnecessary because patients vary the traction force merely by pushing their toes to the floor. And the arm rests and supports also enable patients to distribute their weight and effect better relaxation of the trunk muscles.

PURPOSE OF THE INVENTION

The primary purpose of the invention is to provide a traction unit for decreasing inflammation and stress on specific, affected areas of a person's spine for those having severe back conditions and to relieve pain caused by inflammation by the various known disorders affecting the spine as noted above.

Another object of the invention is to provide a traction device having a focusing spinal traction element to direct a gravity force to a selected treatment area along a person's spine to effect thoracic and lumbar pain relief.

A further object of the invention is to provide a traction unit with a simple construction so that it takes up minimal floor space and may be easily used for applying about 40% of a person's weight to stretch the person's spine to relieve back pain.

A still further object of the invention is to provide a traction assembly in which a person being treated may don a harness mechanism about the person's torso and voluntarily step from a non-traction receiving level to a traction receiving position to apply a gravity traction force to a selected inflamed area for a measured time period that is controlled by the person subjected to the traction force.

Another object of the invention is to provide a traction assembly that reduces the amount of time a patient must spend in traction to gain spinal-centered pain relief.

A further object of the invention is to directly treat the inflamed spinal area with focused traction force that produces pain relief regardless of whether the pain emanates from a skeletal, muscular, ligament, or spinal disk disorder.

SUMMARY OF THE INVENTION

The invention comprises a traction assembly that directs a focused traction force specifically to the area of maximal muscle strain and spasm along a patient's spine. This traction force decreases stress on affected areas of the spine and truly allows the affected muscles to relax and stretch thus reducing the inflammatory process that predominantly generates pain.

The vertical traction assembly of the invention uses gravity to stretch a person's spine and comprises frame means and torso harness means coupled to downwardly depend from said frame means. Stand means provide a non-traction receiving surface adjacent said frame means on which a person may step to don the torso harness means. The harness means is effective to suspend the person from the frame means when the person steps from the non-traction receiving surface to a vertical, gravity traction position after donning said harness means. Focused traction force means connected to the frame means is provided for directing traction pressure to a selected location along the spine of a person in said vertical, gravity traction position.

Another feature of the frame means includes backboard means for supporting an upper body portion of the person who is wearing the harness means and is suspended in the vertical, gravity traction position. The backboard means includes focused traction force means for directing traction pressure to a selected location along the spine of a person that is disposed in the vertical, gravity traction position. The focused traction force means is adjustably connected to the frame means to be selectively secured to a plurality of vertical locations for directing a gravity traction force to a preselected area at a point along the spine of a person to be suspended from the frame means.

A further feature of the frame means includes a front rearwardly tilted frame portion including backboard means. Focused traction force means includes pad element means adjustable mounted to the backboard means and releasable fastening means is provided for selectively positioning the pad element means with respect to a person using the assemble to undergo vertical traction treatment in a full suspension position. The focused traction force means is effective to direct a traction force equal to a fraction of the person's weight at a selected location along the spine of a person undergoing a full vertical, gravity traction suspension. In a specific embodiment, the traction force is equal to about 40% of the person's weight.

Moreover, the focused traction force means is effective to direct a first traction force equal to about 20% of a person's weight at a selected location along the spine of a person standing on a partial traction receiving surface. A second traction force equal to about 40% of a person's weight is then directed to a selected location along the spine of a person undergoing a full vertical, gravity traction suspension.

A traction method of the invention treats an inflamed area adjacent a person's backbone and comprises providing frame means and torso girding means coupled to flexibly depend from said frame means. The patient being treated dons the torso girding means and derives a horizontally directed traction pressure from his or her weight when the person is in a vertical, gravity traction suspension position. The horizontal traction pressure is applied directly to the inflamed area along the spine of the person while suspended in the vertical, traction suspension position. In a specific embodiment of the method invention, the traction pressure is applied according to a protocol that includes a treatment cycle having a plurality of abbreviated traction sessions in which the patient is suspended in the vertical traction suspension position. The traction sessions are separated with respect to each other with a rest period without traction. More particularly, each said traction session has a duration of up to 90 seconds and each rest period has a duration of up to 90 seconds. And the traction pressure is equal to about 40% of the patient's body weight.

A traction assembly of the invention comprises a frame structure and harness means effective to gird the torso of a person. The torso harness means is coupled to flexibly depend from the frame structure to suspend the person from the frame structure in a vertical, gravity traction position. Focused traction force means is adjustable connected to the frame structure for horizontally directing traction pressure to a desired selected location along the spine of a person in the gravity traction position. A feature of the invention is directed to a backboard mounted to the frame structure and disposed at a tilt angle with respect to the vertical. The tilt angle used is based on physics calculations and data retrieved in clinical trials.

In a specific embodiment, the traction force means includes a spinal pressure element means for applying a portion of the patient's weight to a single focused traction area at a selected point along a patient's backbone that reduces pain-causing stress on the affected spinal area. The selected point may be generally referred to as an inflamed area. The patient's lower body freely suspends from the frame structure to allow for subtle side-to-side shifts in the patient's weight that produce a "balanced suspension" that increases the pull on tighter muscles. Depending on the amount of spasm present, the traction force draws up and shortens the tight muscles predominately on the affected side. So the hanging legs cause the side with the shortest muscles to take the bulk of the traction force thereby causing shorter muscles to be pulled harder and elongated. In short, the side undergoing the most spasm will receive the most force and benefit.

Another feature of the vertical traction assembly of the invention includes stand means mounted to the frame means for providing a non-traction receiving surface on which a person may step to don the torso harness means and a partial traction receiving surface. The harness means is effective to suspend the person from the frame means for less than full traction obtained in a full vertical, gravity traction suspension position when the person steps from the non-traction receiving surface to the partial traction receiving surface after donning said harness means.

Little preparation is required for an individual to use the traction assembly of the invention. Patients simply adjust the harness to fit their particular body size and don it on their torso while standing on a platform elevated with respect to the floor so that no traction is produced. Once the torso harness is secured to the frame and their body, patients gradually lower themselves into a suspended position for a traction session for a period of up to 90 seconds. Initially, a traction session may last from 20 to 30 seconds with the time in a suspended position building up to about 1½ minutes depending on the comfort and stress imposed on a patient's backbone.

Clinical tests show that satisfactory results are often achieved using a particular protocol according to the invention. The protocol comprises a single treatment cycle composed of three (3) traction sessions of 20-30 seconds each separated by 30-90 second rest or non-traction periods. As patients are able to withstand longer stays in suspension with continued treatment, the time in traction may increase toward a 90 second duration. This treatment cycle of a series of short traction periods is repeated three alternate days a week for three weeks. Further treatment is effected on a case-by-case basis and depends on such factors as the patient's weight, physical condition, the extent of spinal damage prior to initiating traction treatment, emotional stability, and the degree of pain relief experienced using the traction assembly of the invention. A patient using the traction assembly of the invention often receives immediate relief, which is cumulative with repeated use. But a cautious and conservative treatment program is encouraged. Prolonged time in traction and/or excessive use of the device is discouraged.

BRIEF DESCRIPTION OF DRAWINGS

Other objects of this invention will appear in the following description and appended claims, reference being made to the accompanying drawings forming a part of the specification wherein like reference characters designate corresponding parts in the several views.

FIG. 1 is a front perspective view of a traction assembly made in accordance with the invention;

FIG. 2 is a side perspective view of the assembly shown in FIG. 1;

DESCRIPTION OF SPECIFIC EMBODIMENTS

Figure 3:
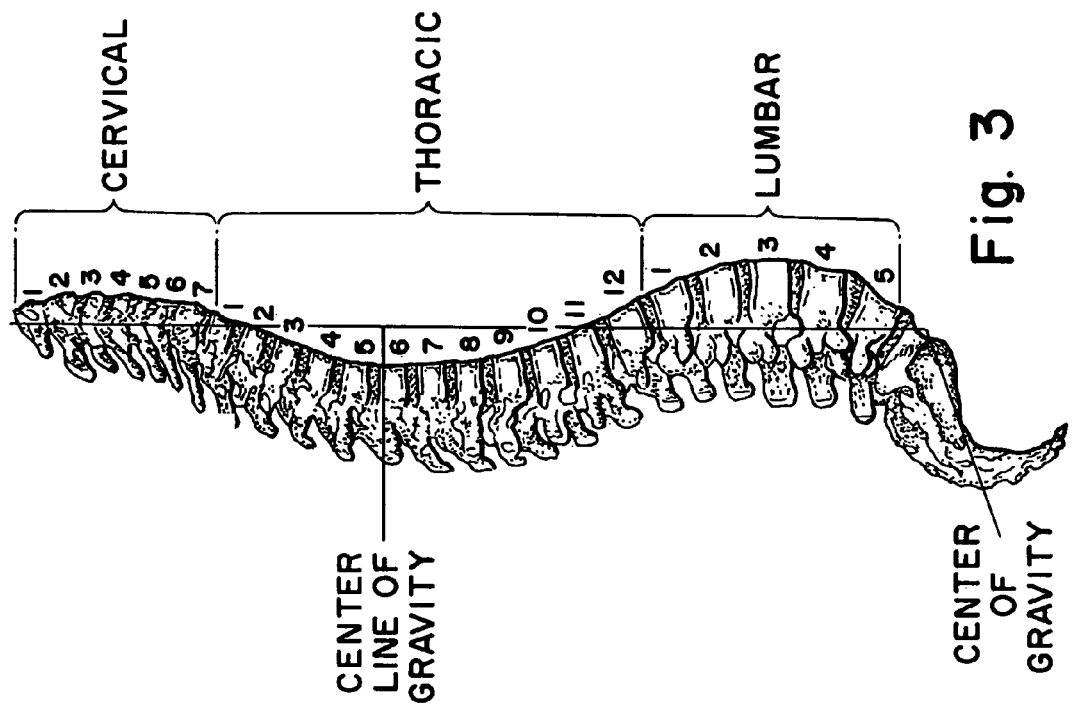
FIG. 3 is a side elevational view of a human backbone.

Traction assembly, generally designated 10 in FIGS. 1 and 2, includes a frame structure 11 having a front portion 20 and a rear portion 22 each fixedly secured to the other and to main base support elements 14a and 14b of base 12 as shown. Front frame portion 20 includes a backboard 24 fixedly mounted to upper board support member 29 and lower board support member 30. A torso harness 35 is attached to depend from upper frame cross-rail member 32. Traction focusing pad element 25 is adjustably mounted to two parallel slots 26 in backboard 24. Threaded stud bolt members project outwardly from the rear of pad element 25 and protrude through slots 26. And wing nut members releasably tighten pad element 25 to enable adjustment along backboard 24 to a desired position where element 25 is disposed adjacent an inflamed area of the patient's spine.

Frame structure 11 is free standing and composed of metal such as aluminum with the frame member connections welded together. The construction of frame structure 11 with cross-rail member 32 is effective to hold in suspension a person weighing up to 350 pounds. Assembly 10 requires about four (4) square feet of floor space and an additional user area in which patients mount and dismount from the unit. Front frame portion 20 is disposed at a rearward slant angle of about 15 to 20 degrees with respect to the vertical direction. At this slant angle, the weight of a patient's legs is focused directly beneath the backbone along a vertical line of gravity and gives a more direct traction pressure on the inflamed and pain affected area when the patient is in a suspended traction position. When a patient is in a fully suspended position, his back is not secured to backboard 24. So his upper body is at an angle of about 13 degrees to the vertical direction because the patient's shoulders come forward with respect to backboard 24 and his upper body is more vertically disposed upon stepping into a fully suspended position.

In this embodiment, front portion 20 is at a 17 degree angle to the normal. Backboard 24 is composed of either ½ inch thick finished plywood or an aluminum panel having a thickness of about ¼ inch or less and is about ten (10) inches wide. Backboard 24 slants rearwardly with front portion 20, has a bottom edge spaced 31 to 36 inches upwardly from the floor, and extends another 35 inches vertically from the floor with slots 26 extending 14 inches vertically. Traction focusing pad element 25 is about 6 inches long to extend across slots 26 to distribute traction pressure transversely across a patient's spinal column. Pad element 25 is composed of resilient padding material and protrudes outwardly from backboard 24 by a distance of about 2 to about 4 inches. A greater distance between the outer engaging surface of pad element 25 and backboard 24 is effective to treat patients having curvature of the spine. Where there is no curvature, a smaller pad element may be used. In a specific embodiment, pad element 25 extends outwardly from backboard 24 for about 3½ inches. Traction pressure focuses at the point where pad element 25 bears against an inflamed area along the patient's backbone and is equal to about 40% of the patient's total weight.

Figure 4:
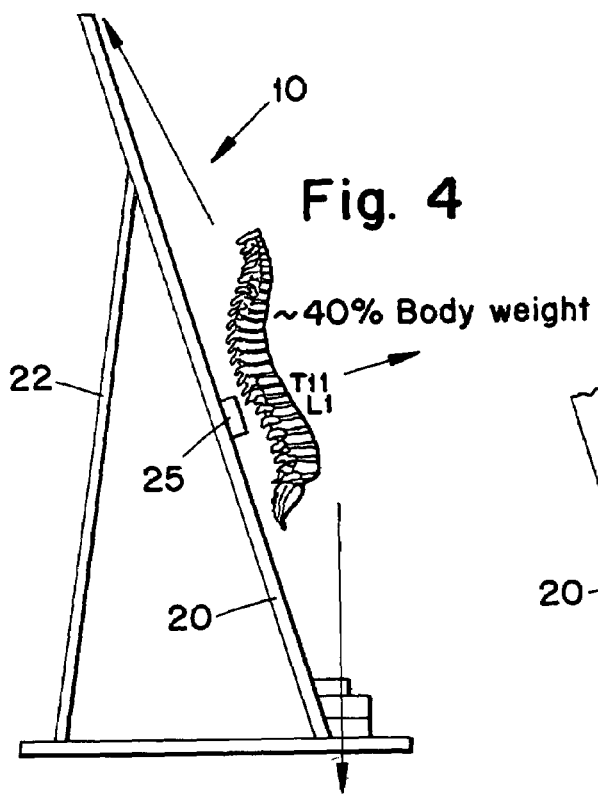
FIGS. 4, 5, 6, and 7 are diagrammatic side elevational views of the disposition of a backbone of a patient with the focusing pad element placed at two different locations along the backboard of an assembly in accord with the invention.
Figure 5:
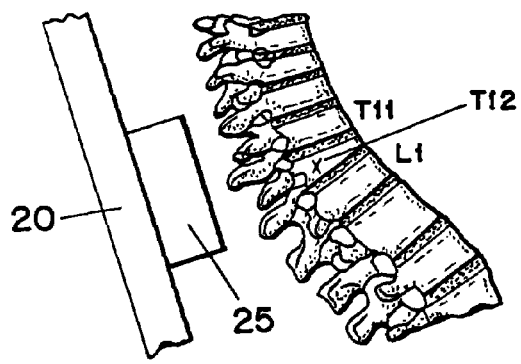
Figure 6:
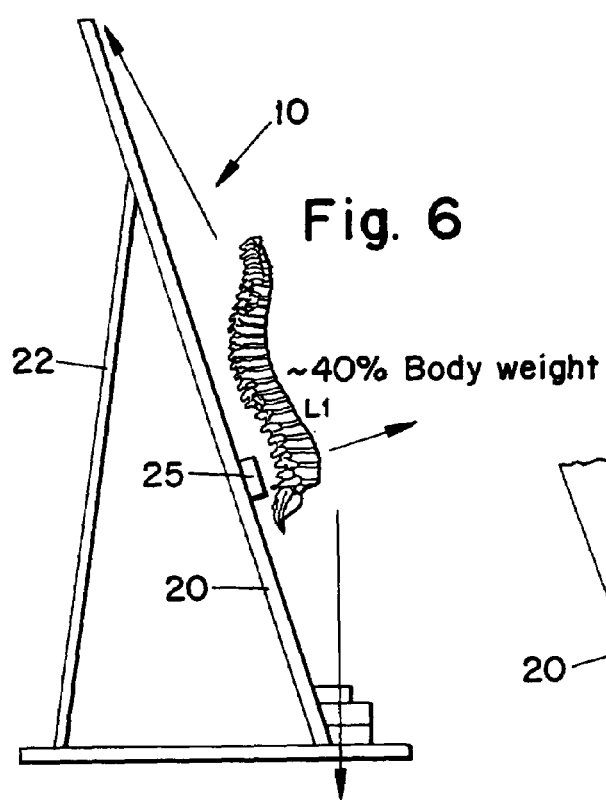
Figure 7:
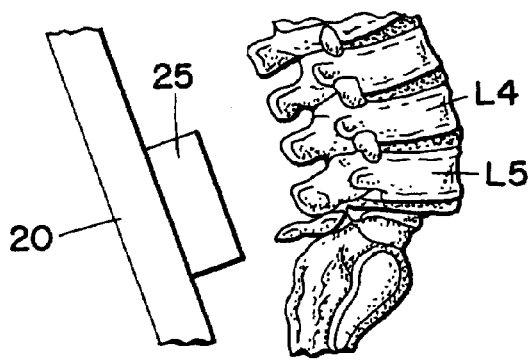

A theory concerning the human backbone and known bone and disk relationships in normal and injured spinal column is helpful in understanding the function of traction focusing pad element 25. FIG. 3 shows a normal human backbone with lumbar (L), thoracic (T), and cervical (C), bone sections separated by disks. The line and center of gravity are shown with respect to the entire human backbone. FIGS. 4 and 5 show pad element 25 placed adjacent the spinal area to focus traction pressure outwardly against bone sections L1, T12, and T11. As shown in FIG. 5 bone T12 has a so-called wedge fracture and during a suspension event, applied traction pressure at the fracture site opens the front edge of the crushed bone T12 to enhance relief of pain and return to a normal relationship with respect to the adjacent disks and bone sections L11 and T12. FIGS. 6 and 7 show pad element 25 at a lower position on backboard 24 adjacent the bottommost lumbar sections L4 and L5 where the spinal curvature is outwardly directed with respect to element 25. Where a lumbar bone section is slipped out of a normal position, the directed traction pressure of element 25 allows it to slide back into place when the person hangs against it during a traction suspension event. In most cases associated with back pain, the disks between bone sections are degenerative under compression. So the idea of traction focusing element 25 is to reduce the area of compression and thus relieve the pressure to enhance restoration of a normal condition.

Pad element 25 provides a horizontal place of impact that is transverse to the spinal column so element 25 is horizontally elongated with respect to the floor to extend across muscles located on either side of the backbone. So pad element 25 has an elongated horizontal length of about six (6) inches and a width of about two (2) inches to extend vertically along the patient's backbone. Pad element 25 may be constructed of layers of carpeting on a base member to produce a focusing area of about two (2) by six (6) inches across the patient's spinal column to encourage the spine to return to a more natural, noninflammation position for its bones sections and disks. The size of element 25 is important because if the focusing area is too small the push of the traction pressure may be too intense. And if it is too large, the traction pressure may be dissipated over too great an area to detract from its usefulness.

The focusing area of element 25 is designed to apply about 40% of the patient's body weight to the spinal column and adjacent muscular structures for urging the spine curvature to a more natural curvature that causes the backbone sections and disks to assume a normal relationship with respect to each other. Cinch strap 36 is adjustably connected to and depends from cross-rail support 32 to control the distance the patient's upper body moves forward from backboard 24 when stepping into a fully suspended position. So the relationship between the patient's disposition in a fully suspended position and any placement of element 25 along backboard 24 will produce a traction focusing pressure of about 40% of the patient's weight onto the inflamed area.

The stand, generally designated 16, includes legs 17 mounted to transverse base support elements 15, lower step member 18 and upper step member 19. In this embodiment, the upper surface of step member 18 is seven (7) inches up from the floor and the upper surface of step member 19 is downward slanted rearwardly and eleven (11) inches from the floor along its high edge end. The upper surface of step member 19 is at a non-traction producing height for a patient to don torso harness 35. The upper surface of step member 18 establishes some traction pressure along cinch strap 36 with a smaller amount of the patient's weight being applied against the backbone through pad element 25. In this position, the therapist may make a final adjustment of the location of element 25 with respect to the inflamed area before the patient steps off step member 18 into a full vertical suspension position. In this embodiment, the person experiences about 20% traction with a smaller portion of the person's weight applied to his spine through element 25 while he stands on lower step member 18. The patient steps off the back of stand 16 to assume a 100% traction pressure in a fully suspended position where about 40% of his body weight is not focused against the inflamed area of his spine.

Figure 9:
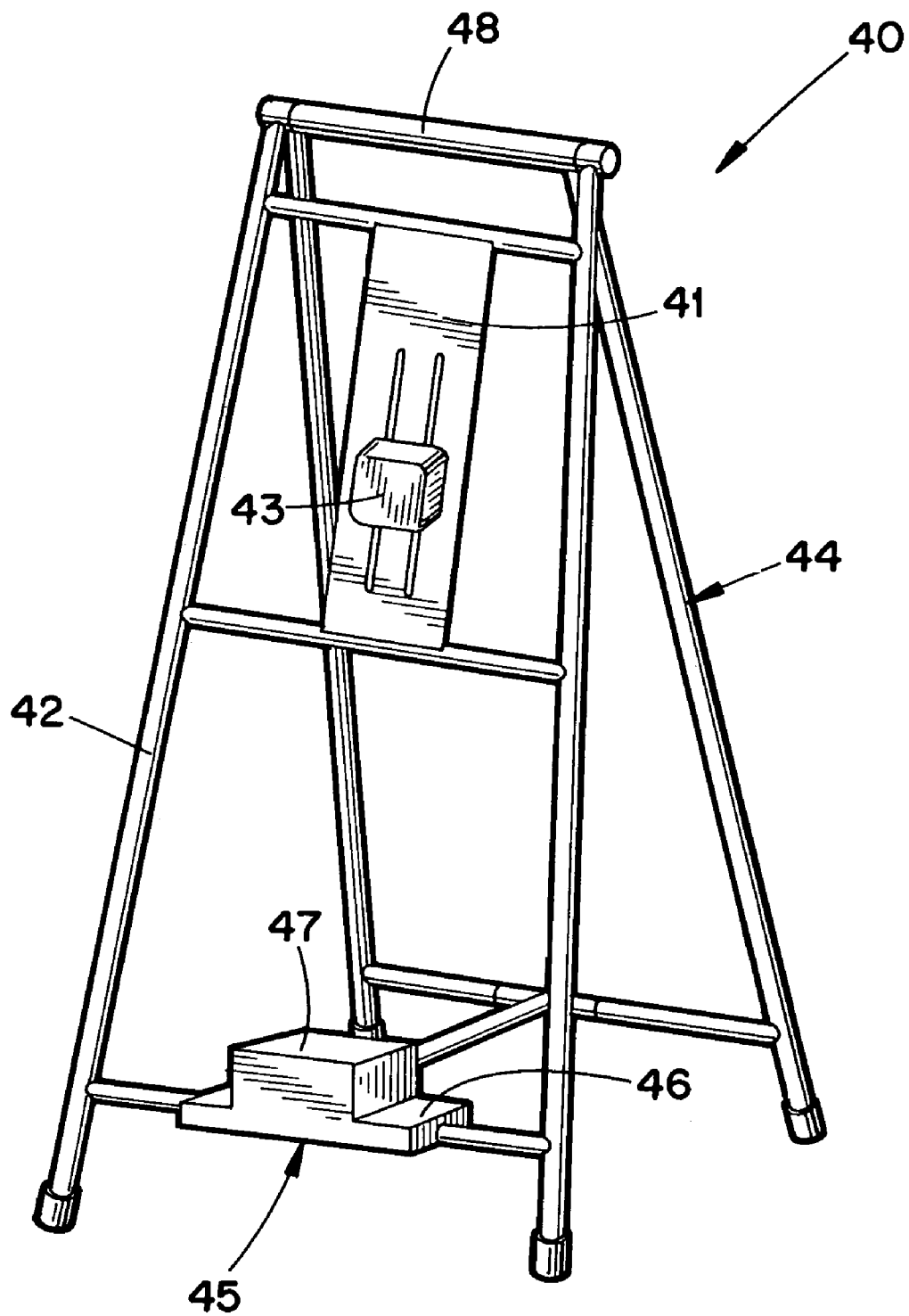
FIG. 9 is a front perspective view of another embodiment of a traction assembly made in accordance with the invention.

FIG. 9 shows another embodiment of a traction assembly 40 of the invention that is portable and may be used in the patient's home. A front frame portion 42 is pivotally connected to rear frame portion 44 to allow them to be folded together. Stand 45 includes two step members 46 and 47 and is constructed to fold upwardly or downwardly and lock into a folded position with respect to front frame portion 42. Once in a folded position as described, assembly 40 becomes portable. Backboard 41 and traction focusing pad element 43 perform identically with respect to assembly 10 as described herein. Harness (not shown) attaches to the cross-rail frame member 48.

The Treatment Protocol

The protocol for treatment of spinal pain comprises the rules of procedure for using the traction assembly of the invention. The spinal pain treatment protocol developed with a specific embodiment of the assembly of the invention enables the patient to undergo minimal traction time when compared to known devices and their related treatment protocols. Known devices are generally used to apply traction over extended periods of time that include extended traction application for several hours while in a horizontal and/or some degree of vertical position. And the patient may continue use of the known traction device application for a period of weeks on end.

In contrast, results experienced by patients using the treatment protocol of the invention prove the effectiveness of the traction assembly of the invention in reducing and, in some cases, eliminating a patient's back pain. The treatment protocol includes an initial treatment segment and a maintenance treatment segment. The initial treatment segment lasts for a plurality of weeks. In this embodiment, the initial treatment segment comprises a three week period that includes three alternate days for each week to effect nine (9) treatment sessions. So in the initial treatment segment a patient would use the traction assembly on a Monday, Wednesday, and Friday or on a Tuesday, Thursday, and Saturday of each of three initial treatment weeks.

Each of the three alternate days includes a single treatment session that may last for a period of 10-20 minutes depending on the facility of the patient and therapist to effect traction treatment with the assembly. The very first treatment generally takes the longest amount of time because the patient must become familiar with the traction assembly. Each subsequent treatment period will be shorter as the patient gains experience in using the assembly. Afterwards, during the maintenance treatment segment, a patient may receive a plurality of once a week treatment sessions for a period of time that will depend on the patient's condition and circumstances. So the maintenance treatment segment time period depends on the subjective feeling of the patient who desires to be free of and maintain freedom from all spinal pain. The number of maintenance treatment sessions is thus determined on a case-by-case basis. For the length of the maintenance treatment segment technically depends on the patient being able to maintain sufficient personal control of spinal order achieved during treatment.

Each treatment session includes a treatment cycle of three vertical suspension events with a rest period after the first and second events. Each suspension event has a duration of from about 20-30 seconds in the first initial treatment segment depending on a patient's capacity to withstand subjection to the traction pressure imposed by gravity. Each intermittent rest period has a duration of about 30 seconds. So once the patient begins the first-suspension event through the third event, the total time expended for a first treatment cycle is about 2 to 2½ minutes. Preparation for suspension to ensure safety and receive the desired benefit from the treatment cycle includes donning and making adjustments to the vest or harness to fit comfortably about the patient's torso, and setting the cinch that connects the vest to the assembly frame and determines the height to which the patient is held above the floor during each suspension event.

Patient preparation for vertical suspension and disengagement after the treatment cycle to loose the patient from the torso harness takes additional time. The overall period for effecting a first treatment cycle may take a total time of from 10-20 minutes. Once the patient grows more accustomed to making the appropriate adjustment settings for donning, suspending from, and disengaging from a vest or harness, the preparation and disengagement periods may be reduced sufficiently so as to reduce the overall time period to be about 5-7 minutes.

The First Office Visit Procedure

X-rays show that a patient complaining of a nagging lower back pain has a disk problem between lumbar bone sections L4 and L5. Inflammation in the area of the disk problem may have involved some soft tissue damage to muscles and ligaments in the area surrounding these bone sections. The patient in this scenario is assumed to be a male in his mid-thirties, 5', 10" tall, and weighs just under 200 pounds. He is questioned as to whether he takes any medication that might affect his ability to withstand the vertical traction suspension. And if he has any prior conditions such as brittle ribs or recent injuries to his upper body it may necessitate additional padding for the harness. Assuming there are no contra indications, the patient proceeds to the traction unit, faces away from unit 10, and climbs to and stands on the upper step where he dons torso harness 35.

The attendant therapist adjusts (a) the length of cinch strap 36 that connects harness 35 to frame 11 to ensure suspension from the floor when the patient steps from the stand, and (b) the height of the traction focusing pad element 25 to a position adjacent the inflamed area around section L4 and L5. The patient puts on the harness and the therapist loosely sets harness 35 in place about his torso with cinch strap 36 located parallel to the patient's backbone. Surrounding straps 37a, 37b, and 37c are placed to direct traction forces proportionately to cinch strap 36. In this embodiment, the strapping is composed of nylon and is not secured in place so that it can adjust to the particular configuration of a patients body structure.

Figure 8:
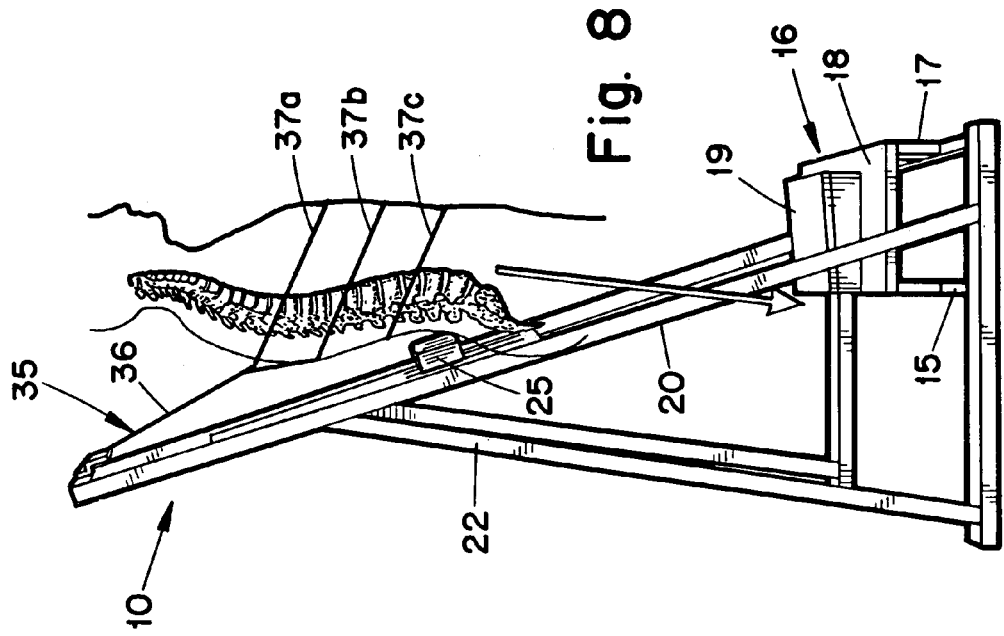
FIG. 8 is a diagrammatic side elevational view of the assembly of FIG. 1 showing the invention's torso harness holding a patient in a fully suspended traction position.

FIG. 8 diagrammatically shows torso harness 35 with cinch strap 36 depending from frame structure 11 holding the patient in a vertical suspension position. Harness 35 includes three belts 37a, 37b, and 37c each having a push-button, quick connect and disconnect buckle to secure it to his torso enabling a quick release if required for any reason. Any obstruction found in the patient's pockets is removed before donning harness 35. The degree of slack in harness 35 relates to the size of the patient, how tight the harness is secured, and the patient's physical shape. Upon the initial adjustment of harness 35, it is secured starting with top belt 37a that is located just under the patient's breast area and is fastened directly in front of him near the solar plexus. The therapist makes sure that the patient has the ability to breath properly. Belts 37b and 37c surround him proportionately and symmetrically. If overweight, lower belts 37b and 37c are set lower to accommodate a larger abdomen. Others who are thin may need additional padding to fill out the belt area. Various types of harness or vest structures are available for similar traction devices as discussed above and may be usable with the assembly of this invention so long as they are capable of gaining the benefits of its novel traction focusing function.

The patient will occupy a different position in harness 35 while suspended that he does while standing on either step of stand 16. In this embodiment, the therapist adjusts the position of pad element 25 so that it is in line with the crest of the hips and adjacent the inflamed area at lumbar section L4 and L5 such as shown in FIGS. 6-8. Such placement of pad element 25 focuses traction force directly on or near the injury to reduce compression of the disk in this area. The patient steps to the lower of the two steps of stand 16 while the therapist adjusts the pad element 25 in anticipation of the position of the patient while suspended during the treatment suspension events. Once pad element 25 is fixed in place and cinch strap 36 is tightened so that the patient's feet will not touch the floor when in a suspended position, the patient is ready to begin his first treatment cycle. The therapist advises the patient of the length of time for each suspension event and that he should engage in deep breathing and relaxation during suspension.

The therapist instructs the patient to step off the back of stand 16 into the unit. The patient my hold on to the vertical frame members of the unit to give him confidence upon stepping off stand 16. In the very first instance of use, his first step from stand 16 into a suspended position is a test and is immediately told to step back onto stand 16. During this beginning test procedure, the patient is learning what to expect from the unit and the therapist may observe the placement of all the settings related to harness 35 and back pad element 25. The patient then again steps off stand 16 for a first 30 second suspension event of the treatment session. He steps back onto stand 16 for a 30 second rest interval and then steps off for a second 30 second suspension event. A second rest interval is then followed by a third suspension event.

Once the third suspension event is complete, the patient steps onto stand 16 and harness 35 is removed. Thereafter, the patient lies down on a cot, table, or bed for a short period such as 1 to 5 minutes so that the inflamed area can regulate itself after having been decompressed. Lying down solidifies and prolongs the effects of the treatment for the patient. It is preferred that he lie with his knees elevated to take stress of his lower back.

Depending on the patient's pain tolerance, he may increase the amount of time in increments for subsequent treatment sessions for a period of up to one minute and 15 seconds in the suspended position. The second session, for example, may have 45 second suspension events and the third session may have one minute suspension events. In any event, each treatment session should always include a 30 second rest interval between suspension events. In one instance with a female having a small body structure, she was able to tolerate four suspension events each having a duration of 45 seconds.

The traction protocol used with the assembly of the invention has consistently produced immediate positive results. Although the patient may feel that he has received maximum relief from his first session, it is important that he complete the entire three week treatment cycle and a recommended maintenance treatment segment to receive a sustained benefit. Once the affected area returns to a more natural state and the back pain subsides, the maintenance treatment segment including at least one treatment session per week is recommended. Without exception in the initial test stages with the traction assembly of the invention, patients report a significant decrease in morning stiffness and a faster recuperation time from incidents that cause back spasm.

While the vertical traction assembly and method has been shown and described in detail, it is obvious that this invention is not to be considered as limited to the exact form disclosed, and that changes in detail and construction may be made therein within the scope of the invention without departing from the spirit thereof.

Having thus set forth and disclosed the nature of this invention, what is claimed is:

1. A vertical traction assembly for using gravity to stretch a person's spine, said assembly comprising:
    a) standing frame means and torso harness means coupled to depend downwardly from said frame means,
    b) said harness means being effective to maintain a person in a vertical traction suspension position after the person dons said harness means, and
    c) traction force focusing means attached to the frame means for applying a focused traction pressure directly to a selected location along the spine of the person who is in said vertical traction suspension position.

2. An assembly as defined in claim 1 wherein said standing frame means includes non-traction receiving surface means on which a person stands for donning the torso harness means before assuming said vertical traction suspension position and applying said focused traction pressure.

3. An assembly as defined in claim 2 wherein said focused traction pressure is derived from the weight of the person who is in said vertical traction suspension position.

4. An assembly as defined in claim 3 wherein said focused traction pressure is equal to about 40% of said person's weight.

5. An assembly as defined in claim 2 wherein said standing frame means further includes a partial traction receiving surface on which the person to be maintained in said vertical traction suspension position may stand to effect adjustment of the harness means with respect to the frame means and the person's torso before said person is subjected to a full traction treatment, said harness means being effective to produce a partial traction treatment pressure equal to a desired percentage of a full traction treatment pressure when the person steps from the non-traction receiving surface to said partial traction receiving surface after donning said harness means.

6. An assembly as defined in claim 5 wherein said desired percentage is about 20% of the full traction treatment pressure which is equal to about 40% of the weight of the person who is in the traction position.

7. An assembly as defined in claim 1 wherein said frame means is free standing and said traction force focusing means being effective to derive said focused traction pressure from a portion of the weight of the person in said vertical traction suspension position with said person being vertically suspended with the harness means to produce said focused traction pressure.

8. An assembly as defined in claim 1 wherein said selected location along the spine of the person includes an inflamed area on the person's back.

9. A vertical traction assembly for using gravity to stretch a person's spine, said assembly comprising:
    a) standing flame means and torso harness means coupled to flexibly depend downwardly from said frame means, and
    b) said frame means including a first non-traction receiving surface means for supporting a person while standing to don the torso harness means and a second partial traction receiving surface means for supporting a person while standing to adjust said harness means with respect to the person's torso and assembly before the person voluntarily steps to a vertical, gravity traction suspension position,
    c) said harness means being effective to suspend the person from the frame means for a partial traction pressure when the person stands on said second partial traction receiving surface means after donning said harness means,
    d) said partial traction pressure being less than a full traction pressure that is applied to the person while in said vertical, gravity traction suspension position.

10. A traction assembly for using gravity to stretch a person's spine, said assembly comprising:
    a) freestanding frame means and harness means effective to releasably gird the torso of a person,
    b) said harness means being coupled to flexibly depend downwardly from said frame means to suspend the person from the frame means in a vertical traction suspension position, and
    c) focused traction force means adjustably connected to the frame means for applying traction pressure directly to a selected location along the spine of the person in said vertical traction suspension position.

11. An assembly as defined in claim 10 wherein said frame means includes backboard means for supporting an upper body portion of the person who is girded with said harness means and suspended in said vertical traction suspension position.

12. An assembly as defined in claim 11 wherein said backboard means includes said traction force focusing means having releasable tightening means for selectively securing the traction focusing force means to a plurality of vertical locations along said backboard means.

13. An assembly as defined in claim 10 wherein said frame means includes a front rearwardly tilted frame portion including backboard means, said traction force focusing means includes pad element means adjustably mounted to the backboard means and releasable fastening means for selectively positioning the pad element means with respect to a person's spine before said person is in said vertical traction suspension position.

14. An assembly as defined in claim 10 wherein said traction force focusing means is effective to direct a traction force equal to a fraction of the person's weight at said selected location along the spine of said person.

15. An assembly as defined in claim 14 wherein said traction force is equal to about 40% of the person's weight.

* * * * *